April 25, 1972 D. L. ARMSTRONG Plant Pat. 3,132
ROSE PLANT
Filed May 27, 1970
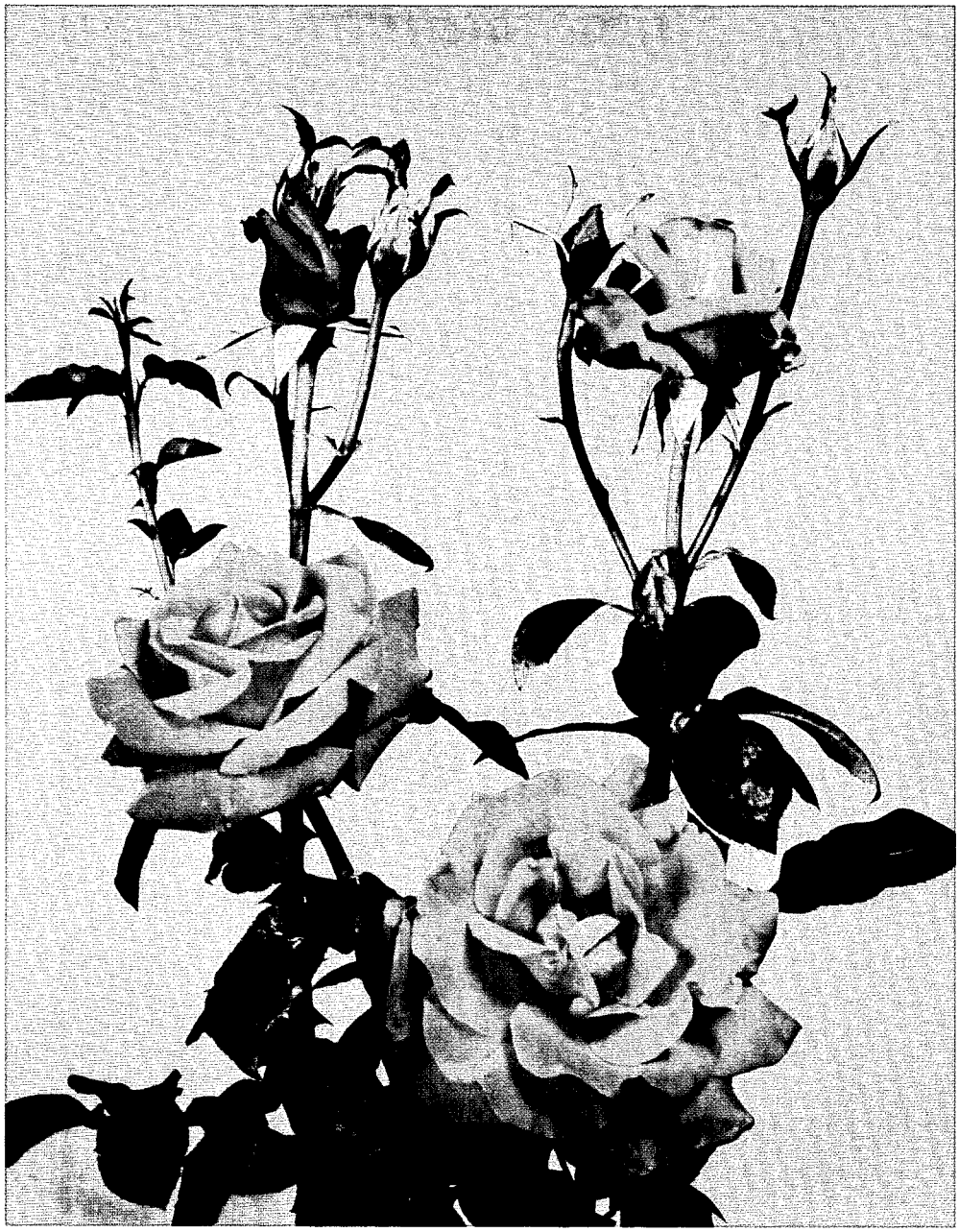

United States Patent Office

Plant Pat. 3,132
Patented Apr. 25, 1972

3,132
ROSE PLANT

David L. Armstrong, Upland, Calif., assignor to Armstrong Nurseries, Inc., Ontario, Calif.

Filed May 27, 1970, Ser. No. 41,121
Int. Cl. A01h *5/00*
U.S. Cl. Plt.—20 1 Claim

ABSTRACT OF THE DISCLOSURE

A hybrid tea rose of upright-spreading and much branched habit, free and vigorous in growth and bearing blooms in great quantity almost continuously during the growing season. More than average resistance to mildew. Flowers borne singly usually but sometimes in clusters of two or three to a stem. Blooms are large and retain their freshness on the bush in the garden for from 6 to 7 days. The flower is cupped on opening; becomes flat with somewhat high-centered-globular interior. Strong purplish red is general color effect.

This invention relates to a new type of hybrid tea rose, a tall bush seedling, well adapted for outdoor cultivation for garden decoration and for cut flower production. Its hardiness in diverse climates has not yet been established. The plant was first grown in Ontario, Calif., as a seedling having for its seed parent Fandango×(World's Fair× Floradora). The pollen parent of this plant was Chrysler Imperial. The plant holds its distinguishing characteristics through succeeding propagations by budding.

As grown in Ontario, Calif., the flowers are usually found singly, but they are sometimes found in regular clusters of two or three, or even more, on strong short to medium stems. The quantity of bloom ranges from very free to abundant outdoors, and blooming is nearly continuous throughout the growing season. The fragrance is tea rose to spicy.

The accompanying drawing illustrates the plant in color and shows the flowering thereof from bud to full bloom.

The new variety manifests a number of characteristics which are different from those observed in the parent stock. It differs from the seed parent, an unnamed seedling from a cross (Fandango×(World's Fair×Foradora)), in that it belongs to the hybrid tea class rather than the grandiflora class; and in that it has up to thirty petals, whereas the seedling parent had only 15–20 petals. The flowers of the new variety are most usually borne single to a stem, whereas the flowers of the seed parent are normally borne in clusters of three or more.

The new variety differs from its pollen parent (Chrysler Imperial) in such ways as the following: The flower of the new variety is strong purplish red in color, whereas the bloom of Chrysler Imperial would commonly be referred to as crimson red. The growth habit of the new variety is both tall and wide and densely covered with foliage, as compared to the growth habit of Chrysler Imperial, which is relatively short with moderate foliage cover.

The flower of the present variety may have up to thirty petals, whereas Chrysler Imperial has been found with 40–50 petals per flower. The buds of this new variety are regarded as small for the class. They are of medium length and ovoid in shape. The buds of Chrysler Imperial are larger and longer. The new variety has a moderate fragrance, whereas Chrysler Imperial has a very strong and penetrating fragrance.

The color values given herein are determined with reference to the Nickerson Color Fan put out by Munsell Color Co., except where obviously the ordinary dictionary meaning is intended.

*Bud*

The peduncle is of average length and average caliper, being erect and moderately smooth. There are a few gland-tipped cilia and few prickles. The color is near Moderate Yellow Green, 2.5 GY 5/5, overlaid with Moderate Reddish Brown, 10 R 3/4, in areas exposed to the direct sun.

Before the calyx breaks, the bud is small in size, of medium length and ovoid in form, with tomentum. and a few gland-tipped cilia on the surface of the bud. There are usually slender, entire, bristle-like foliaceous parts extending beyond the tip of the bud for a distance equal to one-fourth or more of its length.

As the calyx breaks, the color is Dark Red, 5 R 3/7, overlaid with Dark Red, 2.5 R 3/7, with veins showing nearly white because of minute hairs present. The inner surface of the sepal carries a fine tomentum, the margins of alternate sepals being lined with this fine wooly tomentum, whereas margins of other sepals are provided with several small stipitate glands and small slender foliaceous parts.

As the first petal opens, it is small in size, of medium length and urn-shaped in form. The color on the outside of the petal is between Strong Purplish Red, 10 RP 4/12, and Deep Purplish Red, 10 RP 3/10, with a very small area at the base which is nearly Brilliant Yellow Green, 2.5 GY 9/8. The inside surface of the petal shows Strong Purplish Red, 7.5 RP 4/11, overlaid with near Strong Red, 5 R 4/12. A small area at the base is near to Brilliant Greenish Yellow, 10 Y 9/9. The bud opens up well and is not retarded or prevented from opening by cold, hot, wet, or dry weather.

*Bloom*

The size of the bloom when fully open is large, ranging from 4"–5". The petalage is double, ranging from 14–30 petals, plus 2–5 petaloids, regularly arranged. The bloom is cupped at first, becoming open to high-centered globular.

The tips of the petals are rolled at first, becoming reflexed later on, at maturity. Throughout, the petals are somewhat loosely cupped. The petals are leathery, with inside velvety and outside shiny. The outside petals are round, usually with one to two small notches. Intermediate petals are round and scalloped, with one to two notches, and the inside petals are nearly oval, scalloped, irregular, with apex rounded and with one to two notches.

The paragraphs immediately following describe color values observed in a flower newly opened in the month of April. The plant had been grown outdoors, in Ontario, Calif.

The outer surface of the outside petal is between Strong Purplish Red, 10 RP 4/12, and Deep Purplish Red, 10 RP 3/10, with a small area at the base which is nearly white. The inner surface of the outside petal shows a small area at the base which is nearly Brilliant Greenish Yellow, 7.5 Y 9/8. The remainder of the petal is Strong Purplish Red, 7.5 RP 4/11, overlaid with near Strong Red, 5 R 4/12, and covered with a velvety sheen.

The outer surface of the intermediate petal is between Strong Purplish Red, 10 RP 4/12, and Deep Purplish Red, 10 RP 3/10, with a small area at the base which is nearly white. The inner surface of the intermediate petal is Strong Purplish Red, 7.5 RP 4/11, overlaid with Strong Red, 5 R 4/12. The petal is also covered with minute hairs which give it a velvety sheen.

The outer surface of the inner petal is between Strong Purplish Red, 10 RP 4/12, and Deep Purplish Red, 10 RP 3/10, with a small area at the base which is nearly Brilliant Greenish Yellow, 7.5 Y 9/8. The inner surface of the inner petal shows a small area at the base which is Brilliant Greenish Yellow, 7.5 Y 9/8, the remainder of the petal being Moderate Purplish Red, 5 RP 5/10, overlaid with Strong Red, 5 R 4/12.

The paragraphs immediately following describe the color values observed in a bloom which had been open for three days, indoors, in the month of April. The plant had been grown outdoors, in Ontario, Calif.

The outer surface of the outside petal was between Strong Purplish Red, 10 RP 4/12, and Deep Purplish Red, 10 RP 3/10, with a very small area at the base which was nearly white. The inner surface of the outside petal was Moderate Purplish Red, 5 RP 4/10, overlaid with Strong Red, 5 R 4/12, and areas of Deep Purplish Red, 7.5 RP 3/9, where they had been exposed to the sun.

The outer surface of the inside petal is nearly Strong Purplish Red, 7.5 RP 4/11, with a very small area at the base which is nearly white. The inner surface of the inside petal is Moderate Purplish Red, 5 RP 4/10, overlaid with Deep Purplish Red, 10 RP 3/10, and with a small area at the base which is nearly Brilliant Greenish Yellow, 7.5 Y 9/8.

The general color effect of the newly open flower is a Strong Purplish Red, 7.5 RP 4/11, overlaid with Strong Red, 5 R 4/12. The bloom after being three days open gives a general color effect which is between Strong Purplish Red, 10 RP 4/12, and Deep Purplish Red, 10 RP 3/10, with a velvet sheen over the exposed petals. The petals drop off cleanly and are not particularly affected in this respect by cold, hot, wet, or dry weather.

The flower on the bush in the garden persists for from six to seven days in the month of September, in the locality named. Cut roses grown outdoors and kept at living-room temperatures will last from four to five days in the month of September.

Reproductive organs

Stamens: The stamens are many, regularly arranged about the pistils, a few of them being mixed with petaloids.

Filaments: The filaments are of medium length, being 5–15 mms. long, and nearly Strong Orange, 2.5 YR 7/10, in color. A few are without anthers.

Anthers: The anthers are of medium size, opening at various times. On the upper side the margins are near Strong Orange, 5 YR 7/11, and the central area is near Brownish Orange, 5 YR 5/8. On the under side, the color is generally Brownish Orange, 2.5 YR 5/9, with a small area at the apex which is near Dark Reddish Orange, 10 R 4/9.

Pollen: The pollen is somewhat sparse, near Dark Orange Yellow, 7.5 YR 6/9, in color.

Pistils: The pistils are numerous, being approximately 100 in number.

Styles: The styles are uneven, short to average length, thin caliper, and bunched. The lower ¾ of the height is near Brilliant Yellow, 2.5 Y 9/9, while the upper 1/4 of the styles is near Strong Purplish Red, 10 RP 4/12.

Stigma: The stigma is near Pale Orange Yellow, 7.5 YR 9/4, in color.

Ovaries: The ovaries usually are all enclosed in the calyx.

Hips: The hips are of average length and globular in form. The full size hip, before maturity, is Moderate Yellow Green, 5 GY 5/6, in color. They are moderately smooth, with thick, fleshy walls.

Sepals: The sepals fall soon. They are of medium length and spear-shaped. Inside, their color is near Dark Red, 2.5 R 3/7, overlaid with a near white tomentum. Outside, their color is near Moderate Yellow Green, 5 GY 5/6, with darker shades near Moderate Olive Green, 5 GY 4/3, on the veins.

Seeds: The seeds are of average number and usually range from medium to large size. There may be 5–20 of them.

*Foliage*

The compound leaves usually comprise three to five leaflets. They are abundant, large, moderately thin, somewhat leathery and semi-glossy in texture. The leaflets are ovoid in shape, with apex subacute, base round and margin simply serrate.

The mature foliage displays upon its upper surface a Moderate Olive Green, 7.5 GY 4/4, overlaid with Grayish Olive Green, 5 GY 3/2. The under surface is Moderate Olive Green, 5 GY 4/3, overlaid between the veins with white from minute hairs. The main veins are near Moderate Purplish Red, 5 RP 4/10.

The young foliage on its upper surface is near Dark Red, 5 R 3/7; on its under surface it is near Dark Red, 2.5 R 3/7.

The rachis is of average size, grooved on the upper side, with some stipitate glands on the edges. The under side is moderately smooth and with stipitate glands.

The stipules are short, moderately narrow, with long point, turning out at an angle of more than 90°.

The plant displays a resistance to mildew which is greater than average in relation to comparable varieties in the same area.

*Growth*

The plant is of upright-spreading habit, much branched. It displays a very free and vigorous growth. The canes are a medium caliper.

The main stems are near Moderate Yellow Green, 5 GY 5/6, in color. They bear a few large prickles which are of medium length, slightly hooked downward, with medium length narrow base. Their color is near Moderate Brown, 7.5 YR 4/5. There are very few small prickles, and their color is the same as that of the large prickles. There are no hairs.

The branches are a near Moderate Yellow Green, 7.5 GY 5/7, color. They carry a few large prickles which are moderately short, almost straight, with short narrow base. The color is near Dark Greenish Yellow, 10 Y 6/7. There are a few small prickles on the branches which are near Dark Greenish Yellow, 10 Y 6/7, in color. There are no hairs.

On new shoots, the color is near Strong Yellow Green, 5 GY 6/8, except in areas exposed to the sun, which are overlaid with Moderate Red, 2.5 R 4/10. There are a few large prickles on the new shoots, these being moderately short, almost straight, with very short narrow base. Their color is near Light Olive, 10 Y 5/5, towards the tip, gradually darkening to near Dark Red, 2.5 R 3/7, at the base. There are a few small prickles on the new shoots, and their coloration is practically the same as that of the large prickles just above described. The new shoots bear no hairs.

I claim:

1. An upright-spreading and much branched rose plant of the hybrid tea class, substantially as shown and described herein, distinguished by combinations of the following characteristics, namely, the scarcity of large prickles on the main stems, such prickles being slightly hooked downward with medium length narrow bases, the plant tending to bear most of its blooms on single, long strong stems, and the remainder in regular clusters of two or three, the bloom being large, of double petalage, slightly cupped at first but becoming somewhat high-centered-globular, and having a moderate fragrance, blending the aroma of tea rose and spice, the general color effect of the flower being strong purplish red.

No references cited.

ROBERT E. BAGWILL, Primary Examiner